(12) United States Patent
Sun et al.

(10) Patent No.: US 11,957,125 B2
(45) Date of Patent: Apr. 16, 2024

(54) CONTINUOUS REFRIGERATION SYSTEM FOR KIDNEY TRANSPLANTATION SURGERY

(71) Applicant: JINGSU TECH-BIO-MED MEDICAL EQUIPMENT CO., LTD., Changzhou (CN)

(72) Inventors: Xun Sun, Changzhou (CN); Yanlin Guo, Changzhou (CN)

(73) Assignee: JINGSU TECH-BIO-MED MEDICAL EQUIPMENT CO., LTD., Jiangsu (CN)

(*) Notice: Subject to any disclaimer, the term of this patent is extended or adjusted under 35 U.S.C. 154(b) by 75 days.

(21) Appl. No.: 17/558,800

(22) Filed: Dec. 22, 2021

(65) Prior Publication Data
US 2022/0110317 A1    Apr. 14, 2022

Related U.S. Application Data

(63) Continuation of application No. PCT/CN2021/073060, filed on Jan. 21, 2021.

(30) Foreign Application Priority Data

| Jul. 15, 2020 | (CN) | 202010681662.5 |
| Dec. 31, 2020 | (CN) | 202011639271.3 |

(51) Int. Cl.
*A01N 1/02* (2006.01)
*A61B 17/00* (2006.01)

(52) U.S. Cl.
CPC .......... *A01N 1/0263* (2013.01); *A01N 1/0273* (2013.01); *A61B 2017/00287* (2013.01)

(58) Field of Classification Search
CPC ................ A01N 1/0273; A01N 1/0263; A61B 2017/00287
See application file for complete search history.

(56) References Cited

U.S. PATENT DOCUMENTS

| 9,707,011 | B2* | 7/2017 | Malkowski | A61B 17/3423 |
| 10,172,641 | B2* | 1/2019 | Wachli | A61B 17/3423 |
| 2008/0008987 | A1 | 1/2008 | Bianco et al. | |

(Continued)

FOREIGN PATENT DOCUMENTS

| CN | 2877673 Y | 3/2007 |
| CN | 201136622 Y | 10/2008 |

(Continued)

*Primary Examiner* — Jonathan M Hurst
(74) *Attorney, Agent, or Firm* — SZDC Law PC (57) ABSTRACT

A continuous refrigeration system for kidney transplantation surgery includes: a kidney bag, an extracorporeal ring and an intracorporal ring. One end of the kidney bag is provided with a bag mouth that allows the kidney and crushed ice to enter the interior of the kidney bag; the extracorporeal ring and the intracorporal ring are spaced on the kidney bag, and a lead-out end is provided both outside and inside the bottom of the kidney bag. A partial length of the kidney bag is supported to form the through circulation passage through which the kidney enters the kidney bag and thus obtaining a carrier for entering the human body, making the operation simple, convenient and fast. The lead-out end is provided so that the kidney bag is adapted to laparoscopic surgery.

11 Claims, 11 Drawing Sheets (56) References Cited

U.S. PATENT DOCUMENTS

| | | | | |
|---|---|---|---|---|
| 2011/0071359 | A1* | 3/2011 | Bonadio | A61B 17/0293 |
| | | | | 600/184 |
| 2017/0049427 | A1* | 2/2017 | Do | A61B 17/00234 |
| 2017/0056065 | A1* | 3/2017 | Do | A61B 17/3423 |
| 2017/0252026 | A1* | 9/2017 | Gupta | A61B 17/3462 |
| 2017/0325800 | A1* | 11/2017 | Prior | A61B 17/00234 |
| 2018/0338773 | A1* | 11/2018 | Parys | A61B 17/3423 |
| 2021/0190405 | A1* | 6/2021 | Sever | F25D 25/005 |

FOREIGN PATENT DOCUMENTS

| | | |
|---|---|---|
| CN | 203724140 U | 7/2014 |
| CN | 107348974 A | 11/2017 |
| CN | 107485458 A | 12/2017 |
| CN | 107969419 A | 5/2018 |
| CN | 109310452 A | 2/2019 |
| CN | 209996379 U | 1/2020 |
| CN | 111824597 A | 10/2020 |
| WO | 2020061495 A1 | 3/2020 |

* cited by examiner

CONTINUOUS REFRIGERATION SYSTEM FOR KIDNEY TRANSPLANTATION SURGERY

This application is a Continuation Application of PCT/CN2021/073060, filed Jan. 21, 2021, which claims priority to Chinese Patent Application Nos. CN 202010681662.5, filed on Jul. 15, 2020, and CN 202011639271.3, filed on Dec. 31, 2020, all of which are incorporated by reference for all purposes as if fully set forth herein.

TECHNICAL FIELD

The present invention relates to the technical field of medical devices, in particular to a continuous refrigeration system for kidney transplantation surgery.

BACKGROUND

At present, compared with open surgery, kidney transplantation surgery, especially laparoscopic or robot-assisted laparoscopic kidney transplantation, is becoming the mainstream trend of kidney transplantation surgery because it has the advantages of less trauma and better wound healing in the later stage. However, in the prior art, due to the small opening of laparoscopic surgery approach, there is no access passage and surgical operation passage designed for the donor kidney to pass through, so it is difficult to keep the kidney in a low temperature environment before and during the operation, which may have an impact on the survival rate of the kidney organ after the surgery.

In view of the above-mentioned problems, the inventor actively carried out research and innovation based on the rich practical experience and professional knowledge in the engineering applications of such products for many years, in order to create a continuous refrigeration system for kidney transplantation surgery and make it more practical.

SUMMARY

The technical problem to be solved by the present invention is to provide a continuous refrigeration system for kidney transplantation surgery, so as to solve the aforementioned problems.

To this end, the present invention provides a continuous refrigeration system for kidney transplantation surgery, for refrigerating the kidney from the beginning of the kidney transplantation surgery to the opening of the renal arteries and veins, comprising: a kidney bag, an extracorporeal ring and an intracorporal ring.

wherein one end of the kidney bag is provided with a bag mouth that allows the kidney and crushed ice to enter the interior of the kidney bag, the bottom of the kidney bag being a closed end;

The extracorporeal ring and the intracorporal ring are spaced on the kidney bag to support a partial length of the kidney bag to form a through circulation passage.

A lead-out end is provided both outside and inside the bottom of the kidney bag to pull the kidney bag into and out of the patient's body during the operation.

Further, an opening is provided on the lower side wall of the kidney bag.

Further, the lead-out end comprises a pull wire with one end fixed on the kidney bag, and a pull ring connected to the other end of the pull wire.

Further, an end of the kidney bag extends outwardly with respect to the extracorporeal ring with a tightening part, the tightening part being sealed and opened by tying and untying of a mouth drawstring and allows the addition of crushed ice when it is open.

Further, a sealing cover is installed on the extracorporeal ring to allow the addition of crushed ice when it is open.

Further, the sealing cover comprises a sealing cover body, an upper cover, and a sealing cover connection part provided between the sealing cover body and the upper cover, wherein the sealing cover body is fixedly connected to the extracorporeal ring and provided with an internal passage through the kidney bag, and wherein the upper cover is flipped relative to the sealing cover body to open and seal the passage within the sealing cover body.

Further, there is provided a funnel that assists the crushed ice to be poured into the kidney bag when the end of the kidney bag is open.

Further, the funnel comprises an outer funnel and an inner funnel, wherein an end of the inner funnel is partially inserted into a passage of the outer funnel, resulting in an overlapping section which fixes the open end of the crushed ice-holding bag body.

Further, the intracorporal ring is installed by a method comprising the following steps:

a step S1 of extending the bottom of the kidney bag into the human body;

a step S2 of arranging the intracorporal ring in parallel with the depth direction of the incision of the human body and inserting the same into the incision, and pulling the lead-out end outside the kidney bag, so that the intracorporal ring enters the human body through the surgical incision of the patient; and a step S3 of pulling the extracorporeal ring to make the intracorporal ring fits inside the skin tissue of the patient to form a snap.

Further, the funnel is connected to the crushed ice-holding bag body by a method comprising the following steps: passing an open end of the crushed ice-holding bag body through the passage of the inner funnel until it is lead out on the side of the overlapping section and folded, wrapping the overlapping section of the inner funnel, and inserting the end of the crushed ice-holding bag body wrapped on the inner funnel into the passage of the outer funnel, whereby the open end of the crushed ice-holding bag body is fixed.

Further, adding crushed ice into the kidney bag comprises the following steps:

a step A1 of fixedly connecting the funnel to the crushed ice-holding bag body;

a step A2 of flipping the upper cover relative to the sealing cover body to realize the process from sealing to opening of the passage in the sealing cover body;

a step A3 of inserting the outer funnel partially into the passage of the sealing cover body; and a step A4 of controlling the shape of the crushed ice-holding bag body and pouring the crushed ice into the kidney bag.

Further, the use method comprises the following steps:

a step B1 of extending the bottom of the kidney bag into the human body, and fixing the kidney bag on the skin tissue of the human body through the extracorporeal ring and the intracorporal ring;

a step B2 of pulling the lead-out end outside the kidney bag to pull the part of the kidney bag containing the transplanted kidney to the surgical site;

a step B3 of cutting an opening in the lateral wall of the kidney bag in the corresponding direction of the renal arteries and veins and the ureter, surgical operations being performed through the opening;

a step B4 of enlarging the opening by means of instruments and moving the counter-sutured kidney from the interior to the exterior of the kidney bag; and a step B5 of pulling the lead-out end inside the kidney bag to pull the kidney bag and the intracorporal ring out of the patient's body.

The advantageous effects of the present invention are explained below.

In the invention, the kidney enters the kidney bag through the circulation passage, thus obtaining a carrier for entering the human body, making the operation simple, convenient and fast. The lead-out end is provided so that the kidney bag can be adapted to laparoscopic surgery, and it is convenient to pull the kidney to the renal anastomosis by pulling the lead-out end outside the bottom of the kidney bag. Moreover, it is possible to pull the kidney bag outside the body by pulling the lead-out end inside the bottom of the kidney bag, and ensure that the donor kidney is in a continuous low temperature environment by adding crushed ice through the mouth of the bag several times.

DESCRIPTION OF THE DRAWINGS

In order to more clearly illustrate the embodiments of the invention or the technical solutions in the prior art, the accompanying drawings to be used in the description of the embodiments or prior art will be briefly described below. It is obvious that the accompanying drawings in the following description are only some of the embodiments recorded in the present invention, and other accompanying drawings can be obtained according to these accompanying drawings without creative work for those of ordinary skill in the art.

Reference numbers: 1. kidney bag; 11. bag mouth; 12. opening; 13. pull wire; 14. pull ring; 15. tightening part; 16. mouth drawstring passage; 17. mouth drawstring; 2. extracorporeal ring; 3. intracorporal ring; 4. sealing cover; 41. sealing cover body; 411. slot; 42. upper cover; 43. sealing cover connection part; 5. funnel; 51. outer funnel; 52. inner funnel; 6. crushed ice-holding bag body.

DETAILED DESCRIPTION

The technical solutions in the embodiments of the present invention will be described clearly and completely in conjunction with the accompanying drawings in the embodiments of the present invention. Obviously, the described embodiments are only a part of the embodiments of the present invention, rather than all the embodiments.

It should be noted that when an element is referred to as being "fixed to" another element, it can be directly on the another element or an intermediate element may also be present. It should be noted that when an element is referred to as being "connected to" another element, it can be directly on the another element or an intermediate element may also be present. The terms "vertical," "horizontal," "left," "right," and similar expressions used herein are for illustrative purposes only and do not mean that they are the only mode of implementation.

Unless otherwise defined, all technical and scientific terms used herein have the same meaning as commonly understood by those skilled in the art of the present invention. The terms used herein are for the purpose of describing specific embodiments only and are not intended to limit the invention. The term "and/or" as used herein includes any and all combinations of one or more of the related listed items.

As shown in FIGS. 1 to 14, a continuous refrigeration system for kidney transplantation surgery, for refrigerating the kidney from the beginning of the kidney transplantation surgery to the opening of the renal arteries and veins, comprises: a kidney bag 1, an extracorporeal ring 2 and an intracorporal ring 3, wherein one end of the kidney bag 1 is provided with a bag mouth 11 that allows the kidney and crushed ice to enter the interior of the kidney bag 1, and the bottom of the kidney bag 1 is a closed end; wherein the extracorporeal ring 2 and the intracorporal ring 3 are spaced on the kidney bag 1 to support a partial length of the kidney bag 1 to form a through circulation passage; and wherein a lead-out end is provided both outside and inside the bottom of the kidney bag to pull the kidney bag 1 into and out of the patient's body during the operation.

Figure 1:
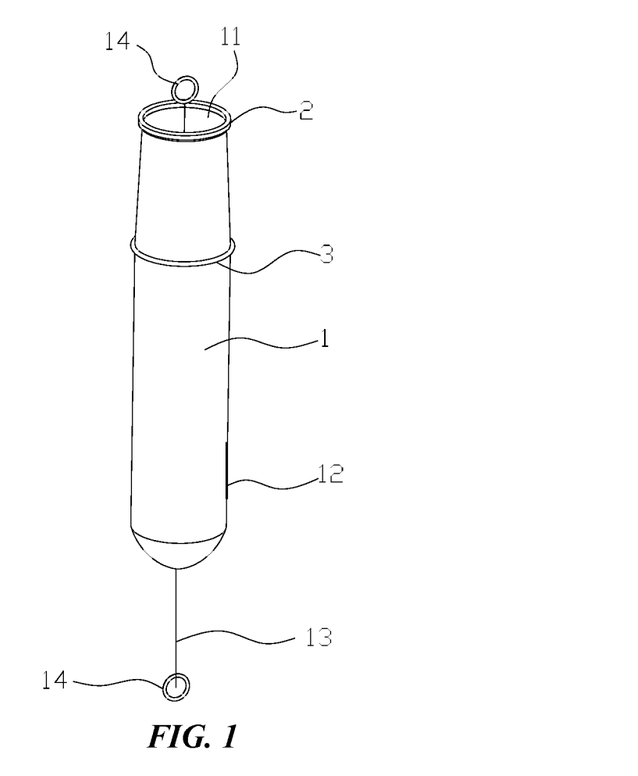
FIG. 1 is a schematic structural diagram of the continuous refrigeration system for the kidney transplantation surgery according to the present invention.
Figure 2:
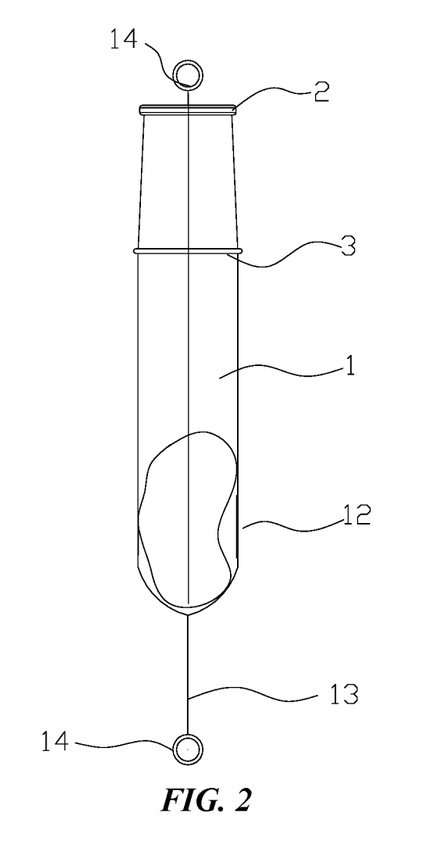
FIG. 2 is a front view of the continuous refrigeration system for the kidney transplantation surgery according to the present invention.

In the invention, a partial length of the kidney bag 1 is support to form the through circulation passage through which the kidney enters the kidney bag 1 and thus obtaining a carrier for entering the human body, making the operation simple, convenient and fast. The lead-out end is provided so that the kidney bag can be adapted to laparoscopic surgery, and it is convenient to pull the kidney to the renal anastomosis by pulling the lead-out end outside the bottom of the kidney bag. Moreover, it is possible to pull the kidney bag outside the body by pulling the lead-out end inside the bottom of the kidney bag, and ensure that the donor kidney is in a continuous low temperature environment by adding crushed ice through the mouth 11 of the bag several times.

Figure 14:
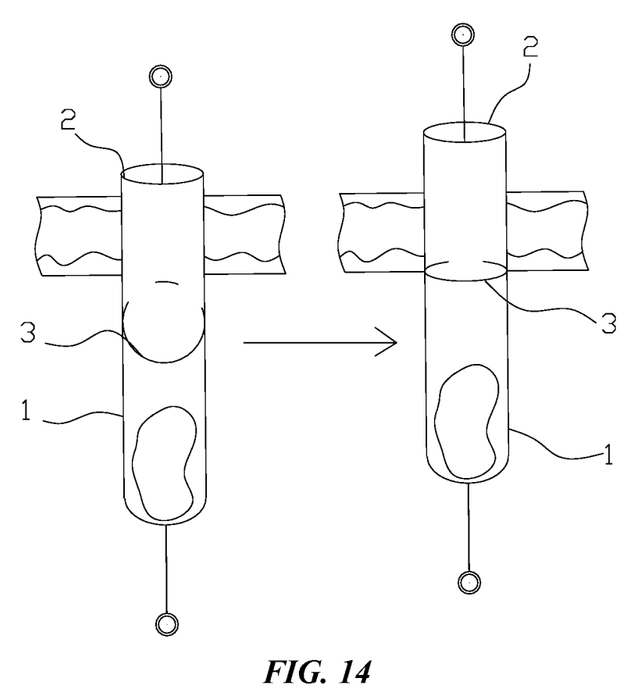
FIG. 14 is a schematic structural diagram of the intracorporal ring forming a snap with the patient's skin tissue according the present invention.

A method of using the aforesaid above-mentioned method of using the continuous refrigeration system for kidney transplantation surgery comprises the following steps:
- a step B1 of extending the bottom of the kidney bag into the human body, and fixing the kidney bag on the skin tissue of the human body through the extracorporeal ring and the intracorporal ring, so that the skin tissue of the human body is supported at the incision to form a passage;
- a step B2 of pulling the lead-out end outside the kidney bag to pull the part of the kidney bag containing the transplanted kidney to the surgical site, where the pulling and the determination of the site need to be done with the help of an external device already extended into the body;
- a step B3 of cutting an opening in the lateral wall of the kidney bag in the corresponding direction of the renal arteries and veins and the ureter, surgical operations such as anastomoses and sutures on the arteries, veins, external iliac arteries, veins and ureters of the transplanted kidney being performed through the opening;
- a step B4 of enlarging the opening by means of instruments and moving the counter-sutured kidney from the interior to the exterior of the kidney bag 1, wherein the size of the opening 12 is not specifically limited as long as it allows smooth removal of the kidney, in this process, the unmelted crushed ice and the liquid resulting from melting will flow out into the human body in a concentrated manner and, again, can be moved out of the body by way of suction;
- a step B5 of pulling the lead-out end inside the kidney bag 1 to pull the kidney bag 1 and the intracorporal ring 3 out of the patient's body, wherein in this process, the bottom of the kidney bag 1 will first move out of the body in the form of a passage formed by the intracorporal ring 3 and the intracorporal ring, and be subsequently removed by pulling the intracorporal ring 3.

Regarding the foregoing embodiment, the intracorporal ring 3 is preferably installed by a method comprising the following steps:
- a step S1 of extending the bottom of the kidney bag 1 into the human body, wherein as far as the method of using the intracorporal ring 3 is concerned, the kidney bag 1 extended into the human body may have already contained the kidney to be transplanted and/or crushed ice, or it has not yet contained the above contents, in which later case the kidney to be transplanted and crushed ice can be provided after the installation of the intracorporal ring 3 is complete;
- a step S2 of arranging the intracorporal ring 3 in parallel with the depth direction of the incision of the human body and inserting the same into the incision, and pulling the lead-out end outside the kidney bag 1 so that the intracorporeal ring 3 is moved towards the body under the pulling of the kidney bag 1, so that the intracorporal ring 3 enters the human body through the surgical incision of the patient, and after the intracorporeal ring 3 enters the human body the original squeezing pressure exerted by the incision is lifted, thus the circular shape of the ring will be restored;
- a step S3 of pulling the extracorporeal ring 2 to make the intracorporal ring 3 fits inside the skin tissue of the patient to form a snap, wherein in order to ensure the effect of maintaining shape of the extracorporeal ring 3 and the extracorporeal ring 2 at the incision, the distance between the extracorporeal ring 3 and the extracorporeal ring 2 can be reduced as much as possible on the premise of meeting the above-mentioned use method.

As a preferred embodiment, an opening 12 is provided on the lower side wall of the kidney bag 1. The opening 12 allows the renal arteries, veins and ureter of the kidney to extend into the patient body to complete the anastomosis operation of the kidney transplantation, thereby saving the time of cutting an opening in the side wall of the kidney bag 1 through the instrument after the kidney enters the human body.

To facilitate operation, the lead-out end comprises a pull wire 13 with one end fixed on the kidney bag 1, and a pull ring 14 connected to the other end of the pull wire 13. The provision of the pull ring 14 increases the force application position during operation, making the pulling of the kidney bag 1 more convenient, lowering the difficulty of operation, and improving the accuracy of the position control of the kidney bag 1.

Figure 3:
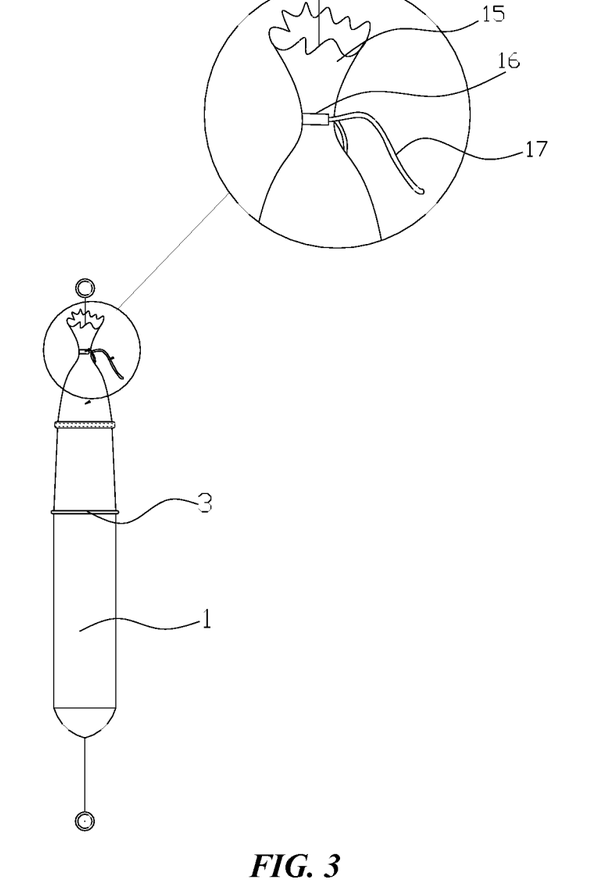
FIG. 3 is a schematic diagram of the optimized structure of the tightening part of the continuous refrigeration system for the kidney transplantation surgery according to the present invention.

During the storage of the kidney, the stability of the environment is favorable for the operation. To this end, an end of the kidney bag 1 extends outwardly with respect to the extracorporeal ring 2 with a tightening part 15, which is sealed and opened by tying and untying of a mouth drawstring 17, and allows the addition of crushed ice when it is open. In order to fix the mouth drawstring 17, a mouth drawstring passage 16 may be provided to form an area for the mouth drawstring 17 to pass through.

As another way of closing the kidney bag 1, a sealing cover 4 is installed on the extracorporeal ring 2 to allow the addition of crushed ice when it is open. The sealing cap 4 is provided so that the interior of the kidney bag 1 can be sealed during the interval of adding the crushed ice, thus effectively ensuring the stability of the kidney refrigeration environment.

Figure 4:
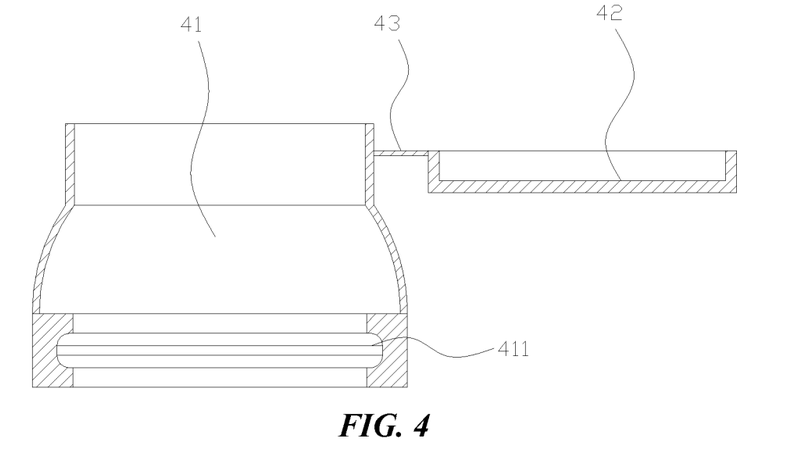
FIG. 4 is a sectional view of the sealing cover according to the present invention.
Figure 5:
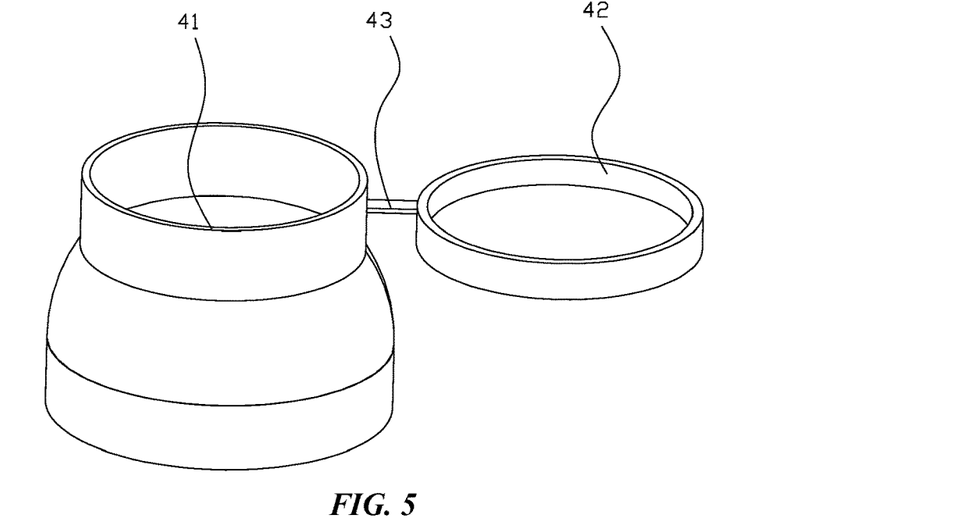
FIG. 5 is a schematic diagram of the structure of the sealing cover according to the present invention.
Figure 6:
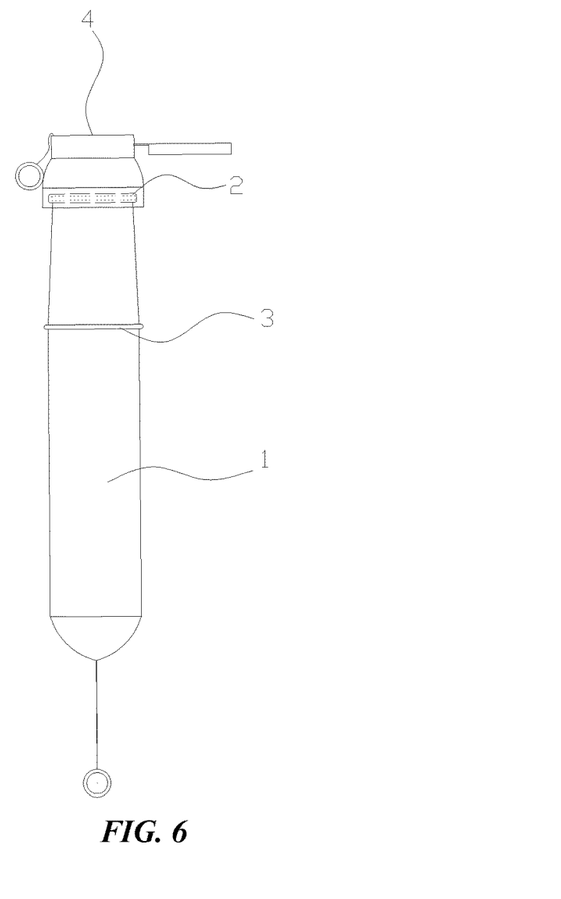
FIG. 6 is a schematic structural diagram of the continuous refrigeration system for the kidney transplantation surgery according to the present invention, with the sealing cover open.
Figure 7:
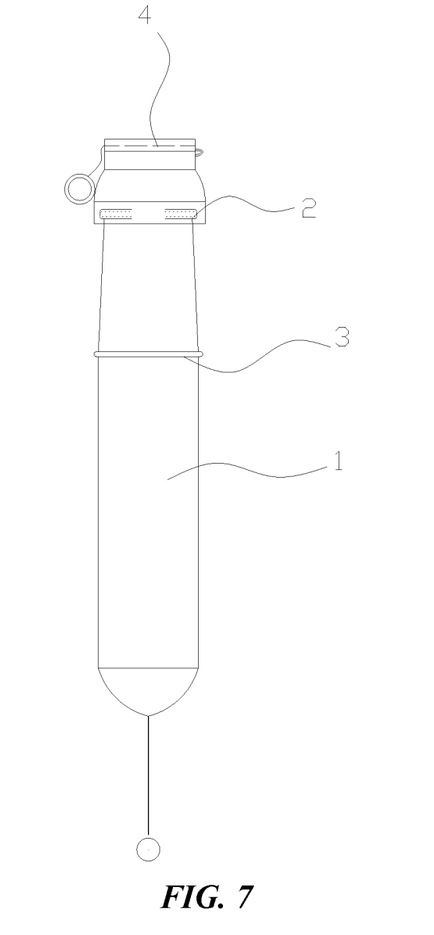
FIG. 7 is a schematic structural diagram of the continuous refrigeration system for the kidney transplantation surgery according to the present invention, with the sealing cover closed.

As a specific implementation, the sealing cover 4 comprises a sealing cover body 41, an upper cover 42, and a sealing cover connection part 43 provided between the sealing cover body 41 and the upper cover 42, wherein the sealing cover body 41 is fixedly connected to the extracorporeal ring 2 and provided with an internal passage through the kidney bag 1, and wherein the upper cover 42 is flipped relative to the sealing cover body 41 to open and seal the passage within the sealing cover body 41.

In the specific implementation, the sealing cover body 41 and the extracorporeal ring 2 can be provided with a slot 411 for the extracorporeal ring 2 to enter, and in use, the extracorporeal ring 2 fits into the slot 411, and the slot 411 forms a limit for the extracorporeal ring 2, which is convenient for installation and removal.

Figure 8:
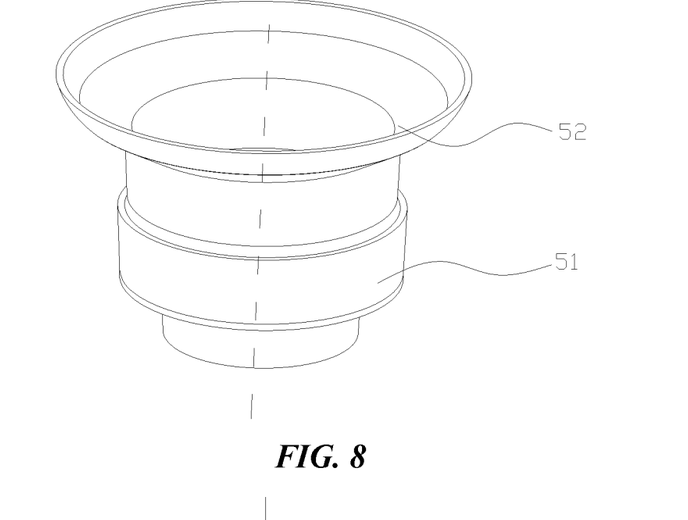
FIG. 8 is a schematic diagram of the structure of the funnel according to the present invention.
Figure 9:
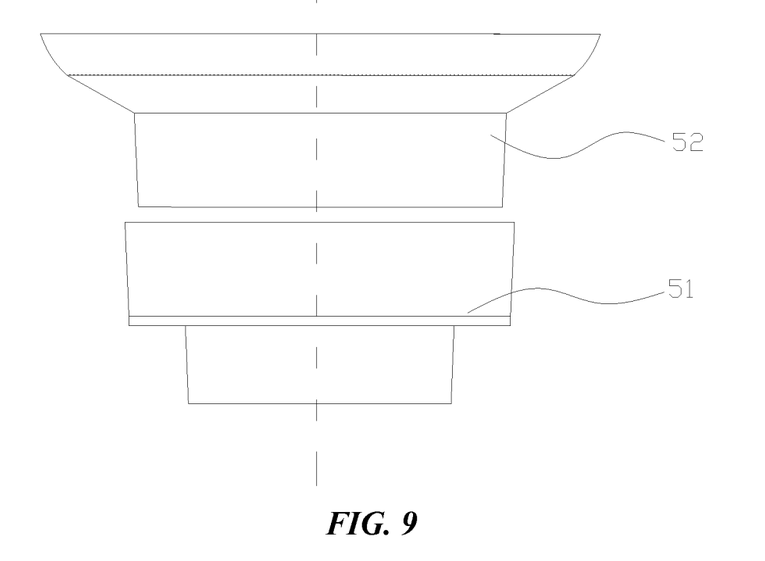
FIG. 9 is a front view of the funnel according to the present invention.

To facilitate the placement of the crushed ice, there is provided a funnel 15 that assists the crushed ice to be poured into the kidney bag 1 when the end of the kidney bag 1 is open.

Figure 10:
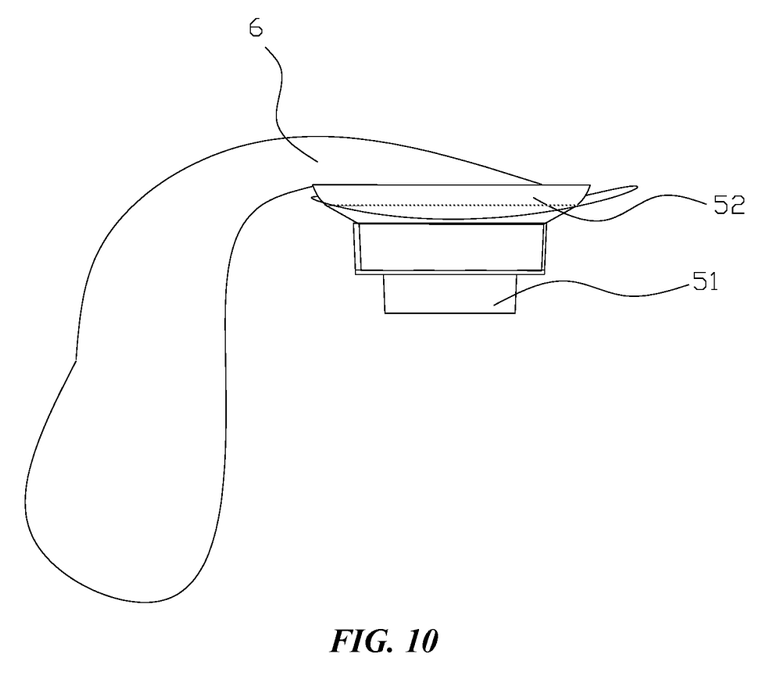
FIG. 10 is a schematic diagram of the connection between the funnel and the crushed ice-holding bag body according to the present invention.
Figure 11:
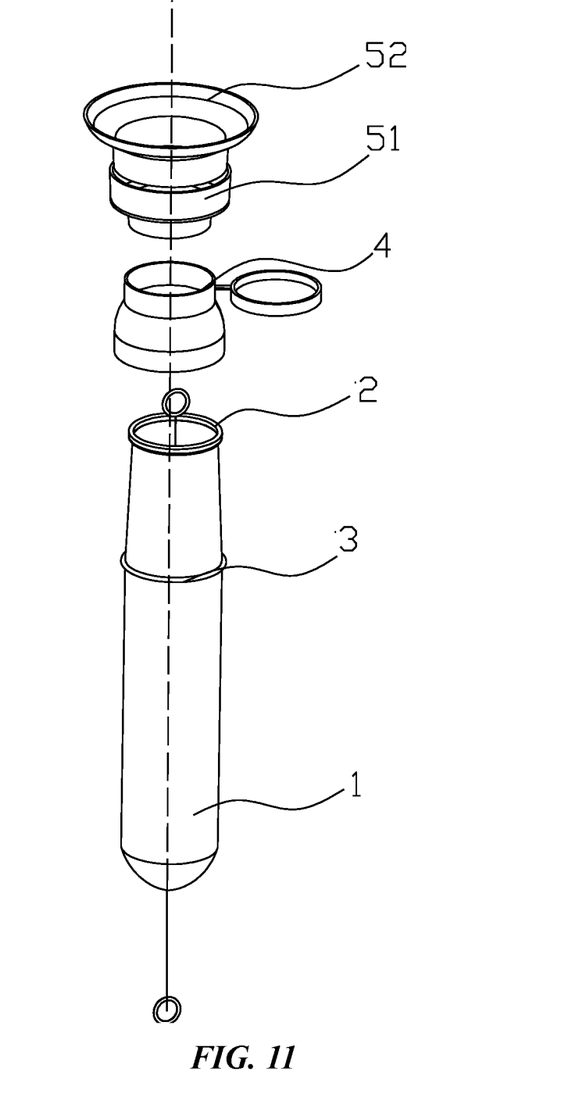
FIG. 11 is an exploded schematic diagram of an optimized structure of the continuous refrigeration system for kidney transplantation surgery according to the present invention.
Figure 12:
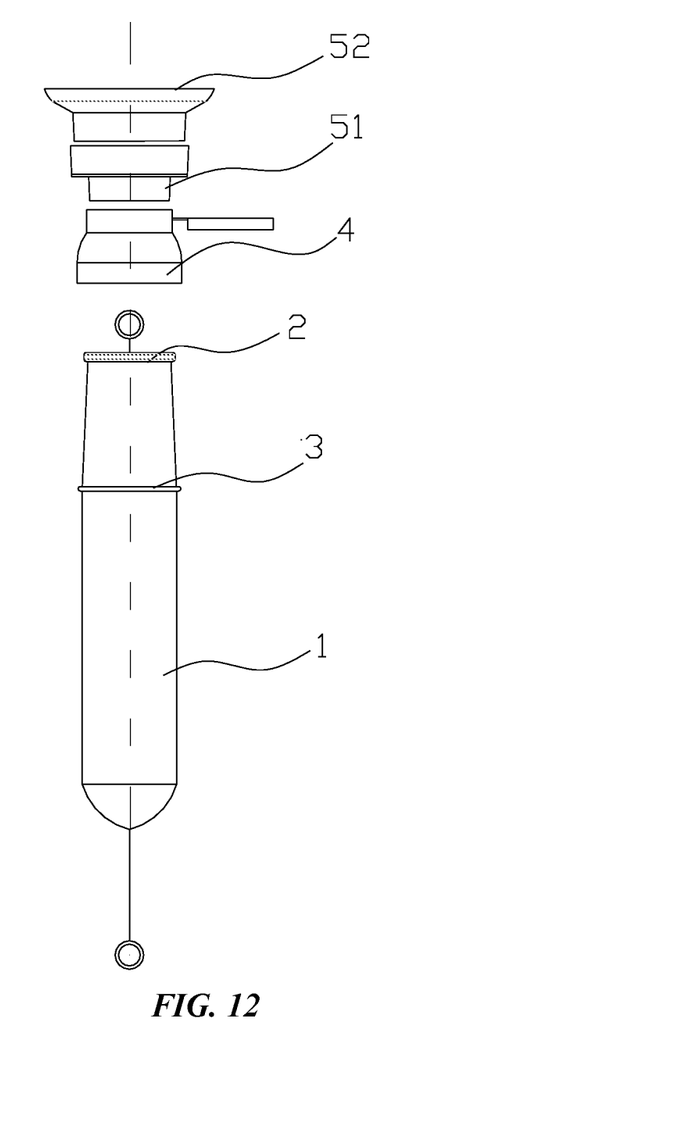
FIG. 12 is an exploded front view of an optimized structure of the continuous refrigeration system for the kidney transplantation surgery according to the present invention.
Figure 13:
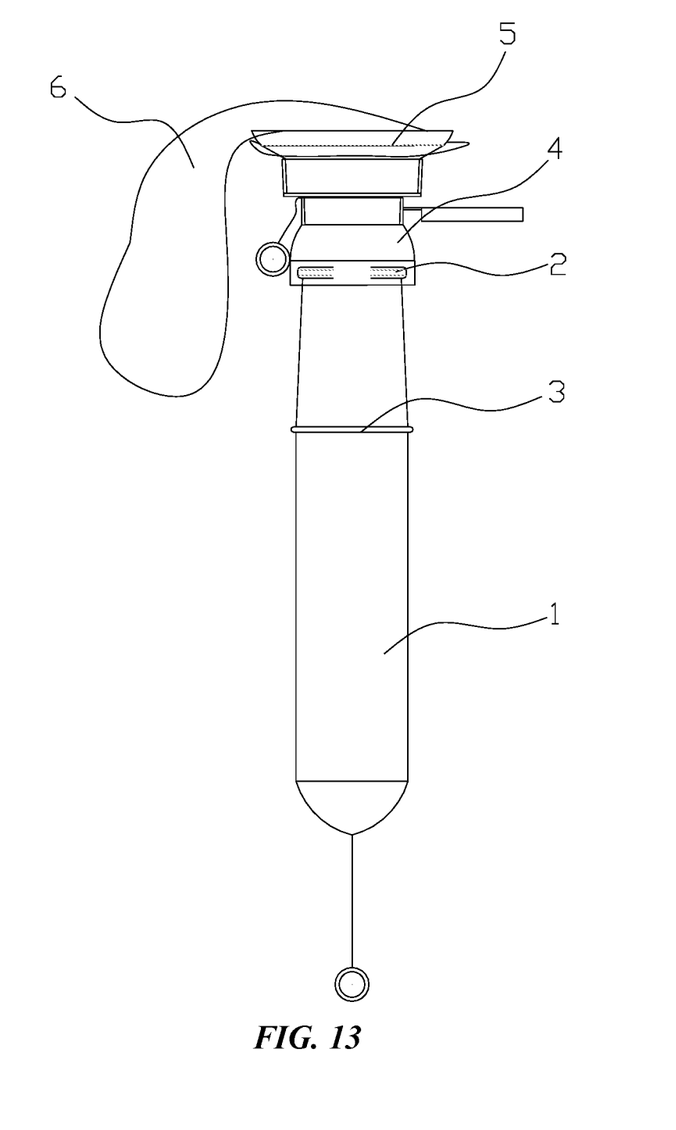
FIG. 13 is a schematic diagram of the connections of various parts of the continuous refrigeration system for the kidney transplantation surgery according to the present invention.

As a specific implementation, the funnel 5 includes an outer funnel 51 and an inner funnel 52. The end of the inner funnel 52 is partially inserted into the passage of the outer funnel 51, resulting in an overlapping section which fixes the open end of the crushed ice-holding bag body 6. The funnel 5 is connected to the crushed ice-holding bag body 6 by a method comprising the following steps: passing an open end 12 of the crushed ice-holding bag body 6 through the passage of the inner funnel 52 until it is lead out on the side of the overlapping section and folded, wrapping the overlapping section of the inner funnel 52, and inserting the end of the crushed ice-holding bag body 6 wrapped on the inner funnel 52 into the passage of the outer funnel 51, whereby the open end 12 of the crushed ice-holding bag body 6 is fixed.

Through the cooperation of the sealing cap and the funnel, adding crushed ice into the kidney bag 1 comprises the following steps:
- a step A1 of fixedly connecting the funnel 5 to the crushed ice-holding bag body 6 in such a manner that the open end of the crushed ice-holding bag body 6 is open;
- a step A2 of flipping the upper cover 42 relative to the sealing cover body 41 to realize the process from sealing to opening of the passage in the sealing cover body 41;
- a step A3 of inserting the outer funnel 51 partially into the passage of the sealing cover body 41, achieving fixing of the two at a relative position by the fit of the inner and outer walls; and
- a step A4 of controlling the shape of the crushed ice-holding bag body 6, raising up the bottom holding the crushed ice to a dumping state so as to pour the crushed ice into the kidney bag 1, wherein the amount of crushed ice to be poured is controlled according to practical demands.

Those skilled in the industry should understand that the present invention is not limited by the foregoing embodiments. The foregoing embodiments and descriptions only illustrate the principles of the present invention. Without departing from the spirit and scope of the present invention, the present invention will have various changes and improvements, which fall within the scope of the claimed invention. The scope of protection claimed by the present invention is defined by the appended claims and their equivalents.

The invention claimed is:

1. A continuous refrigeration system for a kidney transplantation surgery, for refrigerating a kidney from the beginning of the kidney transplantation surgery to the opening of renal arteries and veins, comprising: a kidney bag, an extracorporeal ring and an intracorporal ring,
   - wherein a top end of the kidney bag is provided with a bag mouth that allows the kidney and crushed ice to enter the interior of the kidney bag, the bottom of the kidney bag being a closed end;
   - wherein the extracorporeal ring and the intracorporal ring are spaced on the kidney bag to support a partial length of the kidney bag to form a through circulation passage;
   - wherein a first lead-out end is provided outside the bottom of the kidney bag and a second lead-out end is provided inside the bottom of the kidney bag to pull the kidney bag into and out of a patient's body during the operation, and the second lead-out end extends out the top end of the kidney bag; and
   - wherein an opening is provided on a lower side wall of the kidney bag.

2. The continuous refrigeration system for kidney transplantation surgery according to claim 1, wherein the lead-out end comprises a pull wire with one end fixed on the kidney bag, and a pull ring connected to the other end of the pull wire.

3. The continuous refrigeration system for kidney transplantation surgery according to claim 1, wherein the top end of the kidney bag extends outwardly with respect to the extracorporeal ring with a tightening part, the tightening part being sealed and opened by tying and untying of a mouth drawstring and allows the addition of crushed ice when it is open.

4. The continuous refrigeration system for kidney transplantation surgery according to claim 1, wherein a sealing cover is installed on the extracorporeal ring to allow the addition of crushed ice when it is open.

5. The continuous refrigeration system for kidney transplantation surgery according to claim 4, wherein the sealing cover comprises a sealing cover body, an upper cover, and a sealing cover connection part provided between the sealing cover body and the upper cover, wherein the sealing cover body is fixedly connected to the extracorporeal ring and provided with an internal passage through the kidney bag, and wherein the upper cover is flipped relative to the sealing cover body to open and seal the passage within the sealing cover body.

6. The continuous refrigeration system for kidney transplantation surgery according to claim 5, further comprising a funnel that assists the crushed ice to be poured into the kidney bag when the top end of the kidney bag is open.

7. The continuous refrigeration system for kidney transplantation surgery according to claim 6, further comprising a crushed ice-holding bag body,
   - wherein the funnel comprises an outer funnel and an inner funnel, wherein an end of the inner funnel is partially inserted into a passage of the outer funnel, resulting in an overlapping section which fixes an open end of the crushed ice-holding bag body.

8. The continuous refrigeration system for kidney transplantation surgery according to claim 1, wherein the intracorporal ring is installed by a method comprising the following steps:
   - a step S1 of extending the bottom of the kidney bag into the human body;
   - a step S2 of arranging the intracorporal ring in parallel with the depth direction of the incision of the human body and inserting the same into the incision, and pulling the lead-out end outside the kidney bag, so that the intracorporal ring enters the human body through the surgical incision of the patient; and
   - a step S3 of pulling the extracorporeal ring to make the intracorporal ring fits inside the skin tissue of the patient to form a snap.

9. The continuous refrigeration system for kidney transplantation surgery according to claim 7, wherein the funnel is connected to the crushed ice-crushed crushed ice bag body by a method comprising the following steps: passing the open end of the crushed ice-holding bag body through the passage of the inner funnel until it is lead out on the side of the overlapping section and folded, wrapping the overlapping section of the inner funnel, and inserting the end of the crushed ice-holding bag body wrapped on the inner funnel into the passage of the outer funnel, whereby the open end of the crushed ice-holding bag body is fixed.

10. The continuous refrigeration system for kidney transplantation surgery according to claim 7, wherein adding crushed ice into the kidney bag comprises the following steps:
    - a step A1 of fixedly connecting the funnel to the crushed ice-holding bag body;
    - a step A2 of flipping the upper cover relative to the sealing cover body to realize the process from sealing to opening of the passage in the sealing cover body;
    - a step A3 of inserting the outer funnel partially into the passage of the sealing cover body; and a step A4 of controlling the shape of the crushed ice-holding bag body and pouring the crushed ice into the kidney bag.

11. The continuous refrigeration system for kidney transplantation surgery according to claim 1, wherein the continuous refrigeration system is used by a method comprising the following steps:
    a step B1 of extending the bottom of the kidney bag into the human body, and fixing the kidney bag on the skin tissue of the human body through the extracorporeal ring and the intracorporal ring;
    a step B2 of pulling the lead-out end outside the kidney bag to pull the part of the kidney bag containing the transplanted kidney to the surgical site;
    a step B3 of cutting an opening in the lateral wall of the kidney bag in the corresponding direction of the renal arteries and veins and the ureter, surgical operations being performed through the opening;
    a step B4 of enlarging the opening by means of instruments and moving the counter-sutured kidney from the interior to the exterior of the kidney bag; and
    a step B5 of pulling the lead-out end inside the kidney bag to pull the kidney bag and the intracorporal ring out of the patient's body.

* * * * *